Feb. 22, 1955 C. PETTINGILL Plant Pat. 1,352
APPLE TREE
Filed March 28, 1950
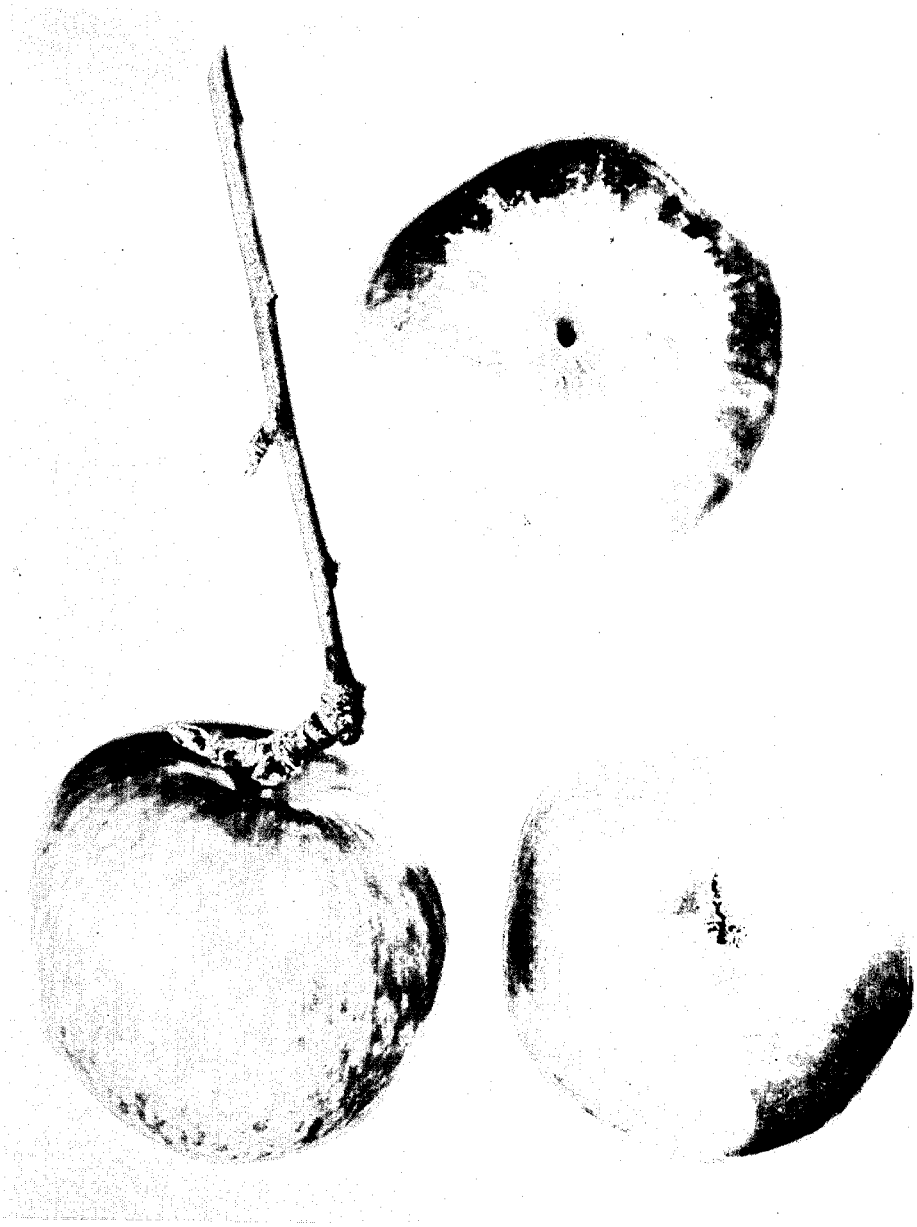
Inventor
Clark Pettingill
By: Robb & Robb
Attorneys United States Patent Office Plant Pat. 1,352

Patented Feb. 22, 1955

1,352

APPLE TREE

Clark Pettingill, Seal Beach, Calif., assignor to Armstrong Nurseries, Inc., Ontario, Calif., a corporation of California Application March 28, 1950, Serial No. 152,309

1 Claim. (Cl. 47—62)

The present invention relates to a new and distinct variety of apple tree originating as a chance seedling of unknown parentage, and discovered by me on my cultivated property at Seal Beach, California.

The most distinct and important characteristic of this new apple is its short dormancy requirement which is even less than that of the variety "Valmore" (Plant Patent No. 238), which is considered among the best suited to Southern California and similar climates where only a short dormancy is experienced.

In combination with this desirable characteristic, the new variety possesses other important and outstanding characteristics, among which are: the large size, stocky trunk, upright and vigorous habits of growth of the tree; very high and regular productivity, with the fruit borne more heavily on terminal buds than on spurs, thus bringing the tree into bearing early in its life; the large, red-skinned fruit, with considerable russet color about the base, and somewhat variable in size and shape, but with an apex which is unique in that it usually is broadly depressed with a round protuberance at the base of each sepal; and a ripening period from early September to mid-October, with keeping quality in cold storage which is superior to that of most summer apples.

Asexual reproduction of this new variety by grafting at Seal Beach, California, shows that the foregoing characteristics come true to form and are established and transmitted through succeeding propagations.

In the accompanying drawing are illustrated obverse views in plan and a side elevation of specimens of the fruit of the new variety.

The following is a detailed description of this new variety, with color terminology in accord with ordinary dictionary significance except where indicated to be in accord with Ridgway's Color Standards and Nomenclature, or Horticultural Colour Chart.

(Observations were made at Seal Beach, California.)

Dates first and last picking—September 1–October 15, 1949.

Tree: Large; vigorous; upright; spreading; open; round; productive; regular bearer.

*Trunk.*—Stocky; medium smooth.

*Branches.*—Medium stocky; medium smooth; brown; semi-glossy. Lenticels—medium in number; medium size.

*Leaves.*—Length of the mature leaf blade, exclusive of petiole, averages about 4 inches with an extreme length of around 5½ inches. Width averages about 2 inches. Nearly oval in shape often approaching an ovate shape, ending somewhat abruptly in an acute tip. Leaf of medium thickness, lightly rugose especially among veinlets. Upper surface glabrous, under surface tomentose.

Color—mature: upper surface—near Cedar Green, Plate VI (Ridgway's); lower surface—near Light Grape Green, Plate XLI (Ridgway's), with midrib near Glass Green, Plate XXXI (Ridgway's). Tomentum on lower surface is Deep Seafoam Green, Plate XXXI (Ridgway's). Leaf new growth—shape of newest growth nearly lanceolate but developing rapidly in width to become nearly orbicular before developing to the mature shape of oval. Tip varying with maturity from acute to only slightly acute. Both surfaces of the blade are covered with a tomentum, the upper surface only slightly, the under surface heavily. The heavy tomentum also covers the petiole and the basal portions of the stipules. The stipules noticeably present only on the new leaf growth are long (1 mm.) and very narrow, turned outward with the tips often recurved. Color—upper surface of newest growth varies from Dull Green Yellow, Plate XVII (Ridgway's) to near Biscay Green, Plate XVII (Ridgway's). Lower surface near Light Fluorite Green, Plate XXXII (Ridgway's).

*Margin.*—Coarsely serrate.

*Petiole.*—Long; 1" to 2"; medium thickness.

Color—mature: Clear Dull Green-Yellow, Plate XVII (Ridgway's), with shadings of Acajou Red, Plate XIII (Ridgway's), near the attachment region; new growth: near Light Turtle Green, Plate XXXII (Ridgway's) with the basal side overlaid with Acajou Red, Plate XIII (Ridgway's).

*Flowers.*—Tends to flower more heavily on terminal buds than on spurs. Date first bloom—April 15, 1949; early.

*Branches.*—Color—varies from near Buffy Olive, Plate XXX (Ridgway's) to near Warm Sepia, Plate XXIX (Ridgway's), which colors are overlaid with a Smoke Grey, Plate XLVI (Ridgway's).

Fruit:

*Maturity when described.*—Eating ripe. Date—September 15, 1949.

*Size.*—Somewhat variable; large.

Diameter axial—2¼ to 3¼ inches.

In transverse plane—2⅛ to 2¾ inches.

*Form.*—Fairly uniform; unsymmetrical, some approaching globular form; most compressed transversely.

Base—nearly truncate; cavity shallowly flaring.

Apex—depressed broadly and prominently with a rounded protuberance at base of each sepal.

*Stem.*—Stout; pubescent; adherence strong.

*Skin.*—Medium thick; medium tender.

Color—underlying color is near Primrose Yellow, Plate 601/1, page 65 (Horticultural Colour Chart), becoming near Uranium Green, Plate 63/2, page 63 (Horticultural Colour Chart), in apex region and deep in the base near the attachment point. Overlying this basic color in blotched form are reddish tones varying from Rhodonite Red, Plate 0022/1, page 188 (Horticultural Chart) to Cardinal Red, Plate 822, page 168 (Horticultural Colour Chart), in the darkest portions. This variation probably due to the amount of exposure to light.

Flesh—Crisp; juicy. Color—near white. Texture—firm; fine; crisp. Ripens—evenly. Flavor—moderately acid. Aroma—distinct. Eating quality—best.

Seed: 9 cm. long, 4 cm. wide at widest point.

*Color.*—Near Amber Brown, Plate III (Ridgway's), overlaid with Chestnut, Plate II (Ridgway's), in basal region.

Use: Market; local; home use.

Keeping quality: Good.

Shipping quality: Good.

I claim:

A new and distinct variety of apple tree, characterized as to novelty by its short dormancy requirement, by the large size, stocky trunk, upright and vigorous habits of growth, by its very high, young bearing and regular productivity, with the fruit borne more heavily on terminal buds than on spurs, by the large, red-skinned fruit with considerable russet color about the base and a broadly depressed base with a round protuberance at the base of each sepal, by its ripening period, and by its superior keeping quality, substantially as shown and described.

No references cited.